United States Patent
Bates et al.

(10) Patent No.: US 9,292,023 B2
(45) Date of Patent: Mar. 22, 2016

(54) DECREASING THE INTERNAL TEMPERATURE OF A COMPUTER IN RESPONSE TO CORROSION

(75) Inventors: Cary L. Bates, Rochester, MN (US); Justin K. King, Rochester, MN (US); Lee Nee, Rochester, MN (US); Michelle A. Schlicht, Rochester, MN (US)

(73) Assignee: International Business Machines Corporation, Armonk, NY (US)

( * ) Notice: Subject to any disclaimer, the term of this patent is extended or adjusted under 35 U.S.C. 154(b) by 825 days.

(21) Appl. No.: 13/612,193

(22) Filed: Sep. 12, 2012

(65) Prior Publication Data

US 2014/0074312 A1 Mar. 13, 2014

(51) Int. Cl.
G05D 23/00 (2006.01)
G05D 23/19 (2006.01)
G06F 1/20 (2006.01)
G01N 17/04 (2006.01)

(52) U.S. Cl.
CPC .............. *G05D 23/1927* (2013.01); *G06F 1/20* (2013.01); *G06F 1/206* (2013.01); *G01N 17/04* (2013.01); *G01N 17/043* (2013.01)

(58) Field of Classification Search
CPC ....... G05D 23/00; G01N 17/04; B65D 35/16; Y10S 148/116
USPC .......................................................... 700/299
See application file for complete search history.

(56) References Cited

U.S. PATENT DOCUMENTS

| | | | | |
|---|---|---|---|---|
| 4,587,479 A * | 5/1986 | Rhoades et al. | ............... | 324/700 |
| 5,208,162 A * | 5/1993 | Osborne et al. | .................. | 436/6 |
| 5,627,749 A * | 5/1997 | Waterman et al. | ................ | 702/6 |
| 6,068,012 A * | 5/2000 | Beardwood et al. | .............. | 137/3 |
| 6,216,235 B1 | 4/2001 | Thomas et al. | | |
| 7,231,318 B2 * | 6/2007 | Kihira et al. | .................. | 702/184 |
| 7,398,184 B1 * | 7/2008 | Chen | ............................. | 702/182 |
| 7,526,944 B2 * | 5/2009 | Sabata et al. | .................... | 73/49.1 |
| 7,861,113 B2 | 12/2010 | Wang | | |
| 2004/0176934 A1 * | 9/2004 | Kihira et al. | ..................... | 703/5 |
| 2005/0122121 A1 * | 6/2005 | Gilboe | ......................... | 324/700 |
| 2005/0126269 A1 * | 6/2005 | Souers | ............................. | 73/86 |
| 2009/0058427 A1 | 3/2009 | Materer et al. | | |
| 2010/0057271 A1 | 3/2010 | Lewis et al. | | |
| 2010/0169251 A1 * | 7/2010 | Cole et al. | ........................ | 706/13 |
| 2012/0038377 A1 * | 2/2012 | Hamann et al. | ............... | 324/700 |
| 2012/0111190 A1 * | 5/2012 | Dariavach et al. | ................ | 95/10 |
| 2012/0176148 A1 * | 7/2012 | Chey et al. | ..................... | 324/700 |
| 2013/0047547 A1 * | 2/2013 | Chey et al. | ..................... | 52/741.3 |
| 2013/0265064 A1 * | 10/2013 | Hamann et al. | ............... | 324/700 |
| 2014/0163903 A1 * | 6/2014 | Klein et al. | ...................... | 702/32 |
| 2014/0306726 A1 * | 10/2014 | Miyazaki et al. | ............. | 324/700 |

FOREIGN PATENT DOCUMENTS

CN 101644654 * 2/2010 ............. G01N 17/02

OTHER PUBLICATIONS

RCS, "Integrated Corrosion Monitoring Systems", Jun. 6, 2009, pp. 2.*
Coles et al, "Air Corrosivity in U.S. Outdoor-Air- Cooled Data Centers is Similar to That in Conventional Data Centers", Mar. 2011, pp. 1-29.*
Muller, "ISA Standard 71.04: Changes Required for Protection of Today's Process Control Equipment", 2011, number of pages 12.*
L. J. Klein et al., "Corrosion Management for Data Centers," IBM Research Report, RC25120, Mar. 8, 2011.

* cited by examiner

*Primary Examiner* — Carlos Ortiz Rodriguez
*Assistant Examiner* — Olvin Lopez Alvarez
(74) *Attorney, Agent, or Firm* — James R. Nock; Owen J. Gamon

(57) ABSTRACT

In an embodiment, a current internal corrosion level at a current time is read from an internal corrosion sensor that is internal to a computer. An internal corrosion difference is calculated between the current internal corrosion level and a previous internal corrosion level. If the internal corrosion difference is more than a first threshold amount, a first action is performed that decreases an internal temperature of the computer.

17 Claims, 4 Drawing Sheets

152 — CORROSION DATA

202 — INTERNAL CORROSION DATA

| TIME (210) | INTERNAL CORROSION LEVEL (212) | INTERNAL CORROSION DIFFERENCE (214) |
|---|---|---|
| 8:00 | .1 | 0 |
| 8:15 | .11 | .01 |
| 8:30 | .15 | .04 |
| 8:45 | .15 | 0 |
| 9:00 | .16 | .01 |
| 9:15 | .25 | .09 |

204 — EXTERNAL CORROSION DATA

| TIME (250) | EXTERNAL CORROSION LEVEL (252) | EXTERNAL CORROSION DIFFERENCE (254) | WIND SPEED (256) | WIND DIRECTION (258) | PREDICTED INTERNAL CORROSION LEVEL (260) |
|---|---|---|---|---|---|
| 8:00 | .2 | 0 | 2 | N | 0 |
| 8:15 | .22 | .02 | 5 | NNE | .15 |
| 8:30 | .28 | .06 | 7 | NNW | .18 |
| 8:45 | .32 | .04 | 4 | ENE | .19 |
| 9:00 | .6 | .28 | 12 | ENE | .22 |
| 9:15 | .7 | .1 | 2 | E | .23 |

FIG. 2

DECREASING THE INTERNAL TEMPERATURE OF A COMPUTER IN RESPONSE TO CORROSION

FIELD

An embodiment of the invention generally relates to computer systems and more particularly to computer systems that detect corrosion.

BACKGROUND

Computer systems typically comprise a combination of computer programs and hardware, such as semiconductors, transistors, chips, circuit boards, storage devices, and processors. Computer hardware is susceptible to damage from corrosion, due to airborne corrosive agents, such as sulfuric acid and nitric acid. Corrosive damage may adversely affect the reliability of the computer and may require computer parts to be replaced, increasing the cost of computer ownership.

SUMMARY

A method, computer-readable storage medium, and computer system are provided. In an embodiment, a current internal corrosion level at a current time is read from an internal corrosion sensor that is internal to a computer. An internal corrosion difference is calculated between the current internal corrosion level and a previous internal corrosion level. If the internal corrosion difference is more than a first threshold amount, a first action is performed that decreases an internal temperature of the computer.

BRIEF DESCRIPTION OF THE SEVERAL VIEWS OF THE DRAWINGS

FIG. 2 depicts a block diagram of an example data structure for corrosion data, according to an embodiment of the invention.

It is to be noted, however, that the appended drawings illustrate only example embodiments of the invention, and are therefore not considered a limitation of the scope of other embodiments of the invention.

DETAILED DESCRIPTION

Figure 1:
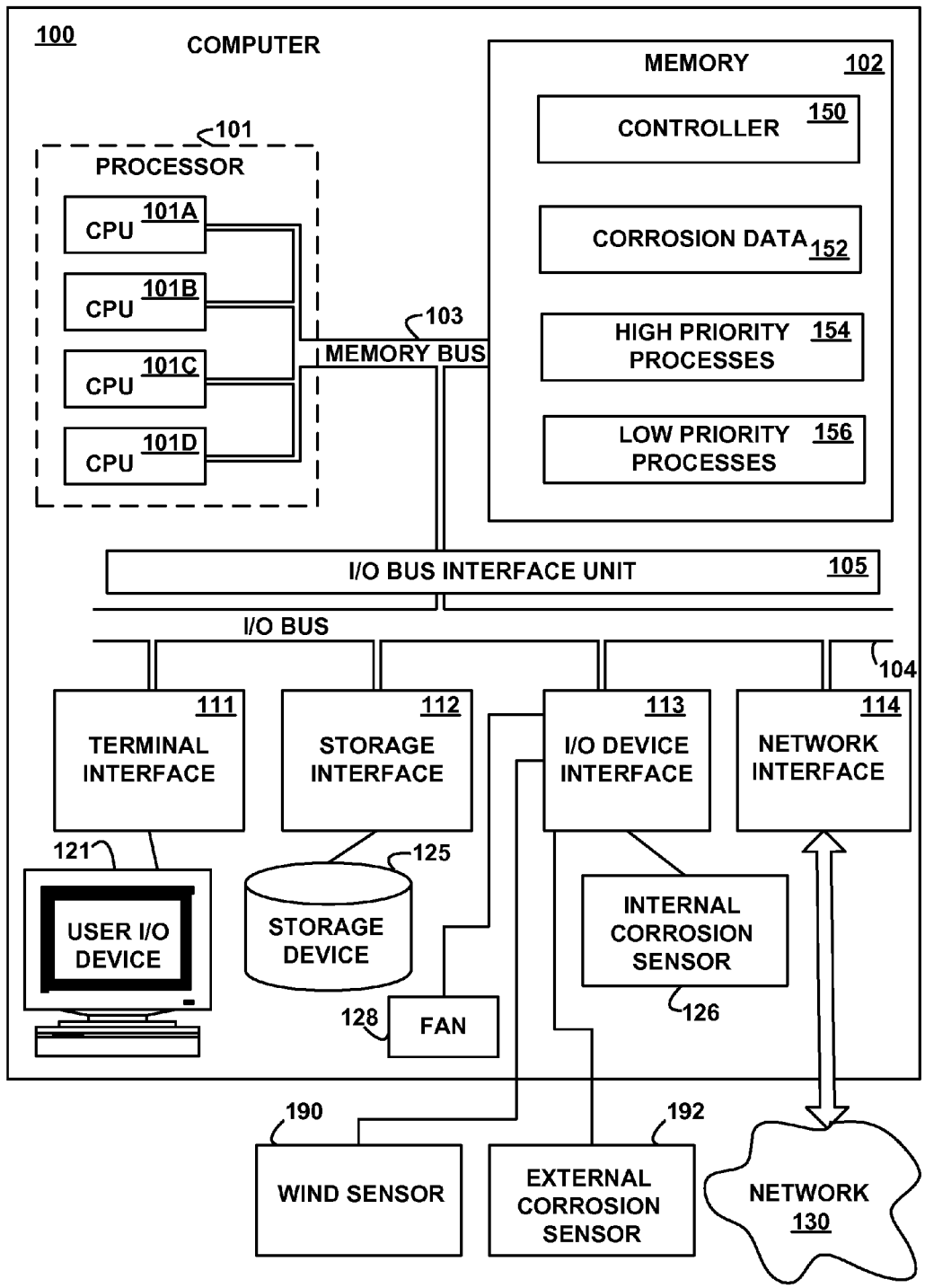
FIG. 1 depicts a high-level block diagram of an example system for implementing an embodiment of the invention.

Referring to the Drawings, wherein like numbers denote like parts throughout the several views, FIG. 1 depicts a high-level block diagram representation of a computer system 100 connected to a network 130, a wind sensor 190, and an external corrosion sensor 192.

The major components of the computer system 100 comprise one or more processors 101, a memory 102, a terminal interface 111, a storage interface 112, an I/O (Input/Output) device interface 113, and a network adapter 114, all of which are communicatively coupled, directly or indirectly, for inter-component communication via a memory bus 103, an I/O bus 104, and an I/O bus interface unit 105.

The computer system 100 contains one or more general-purpose programmable central processing units (CPUs) 101A, 101B, 101C, and 101D, herein generically referred to as the processor 101. In an embodiment, the computer system 100 contains multiple processors typical of a relatively large system; however, in another embodiment the computer system 100 may alternatively be a single CPU system. Each processor 101 executes instructions stored in the memory 102 and may comprise one or more levels of on-board cache.

In an embodiment, the memory 102 may comprise a random-access semiconductor memory, storage device, or storage medium (either volatile or non-volatile) for storing or encoding data and programs. In another embodiment, the memory 102 represents the entire virtual memory of the computer system 100, and may also include the virtual memory of other computer systems coupled to the computer system 100 or connected via the network 130. The memory 102 is conceptually a single monolithic entity, but in other embodiments the memory 102 is a more complex arrangement, such as a hierarchy of caches and other memory devices. For example, memory may exist in multiple levels of caches, and these caches may be further divided by function, so that one cache holds instructions while another holds non-instruction data, which is used by the processor or processors. Memory may be further distributed and associated with different CPUs or sets of CPUs, as is known in any of various so-called non-uniform memory access (NUMA) computer architectures.

The memory 102 stores or encodes a controller 150, corrosion data 152, high priority processes 154, and low priority processes 156. Although the controller 150, the corrosion data 152, the high priority processes 154, and the low priority processes 156 are illustrated as being contained within the memory 102 in the computer system 100, in other embodiments some or all of them may be on different computer systems and may be accessed remotely, e.g., via the network 130. For example, the controller 150, the corrosion data 152, the high priority processes 154, and the low priority processes 156 may be stored in memory in the computers of the network 130. The computer system 100 may use virtual addressing mechanisms that allow the programs of the computer system 100 to behave as if they only have access to a large, single storage entity instead of access to multiple, smaller storage entities. Thus, while the controller 150, the corrosion data 152, the high priority processes 154, and the low priority processes 156 are illustrated as being contained within the memory 102, these elements are not necessarily all completely contained in the same storage device at the same time. Further, although the controller 150, the corrosion data 152, the high priority processes 154, and the low priority processes 156 are illustrated as being separate entities, in other embodiments some of them, portions of some of them, or all of them may be packaged together.

In an embodiment, the controller 150, the high priority processes 154, and/or the low priority processes 156 comprise instructions or statements that execute on the processor 101 or instructions or statements that are interpreted by instructions or statements that execute on the processor 101, to carry out the functions as further described below with reference to FIGS. 2, 3, and 4. In another embodiment, the controller 150, the high priority processes 154, and/or the low priority processes 156 are implemented in hardware via semiconductor devices, chips, logical gates, circuits, circuit cards, and/or other physical hardware devices in lieu of, or in addition to, a processor-based system. In an embodiment, the controller 150, the high priority processes 154, and/or the low priority processes 156 comprise data, in addition to instructions or statements.

The high priority processes 154 have a higher priority than the lower priority processes 156. In an embodiment, any number of priorities may exist. In an embodiment, higher priority processes execute on more or faster of the processors 101 than the lower priority processes and/or receive more processor time. In an embodiment, higher priority processes receive allocations of more memory 102 or other resources (e.g., network bandwidth) than lower priority processes.

The memory bus 103 provides a data communication path for transferring data among the processor 101, the memory 102, and the I/O bus interface unit 105. The I/O bus interface unit 105 is further coupled to the system I/O bus 104 for transferring data to and from the various I/O units. The I/O bus interface unit 105 communicates with multiple I/O interface units 111, 112, 113, and 114, which are also known as I/O processors (IOPs) or I/O adapters (IOAs), through the system I/O bus 104.

The I/O interface units support communication with a variety of storage and I/O devices. For example, the terminal interface unit 111 supports the attachment of one or more user I/O devices 121, which may comprise user output devices (such as a video display device, speaker, and/or television set) and user input devices (such as a keyboard, mouse, keypad, touchpad, trackball, buttons, light pen, or other pointing device). A user may manipulate the user input devices using a user interface, in order to provide input data and commands to the user I/O device 121 and the computer system 100, and may receive output data via the user output devices. For example, a user interface may be presented via the user I/O device 121, such as displayed on a display device, played via a speaker, or printed via a printer.

The storage interface unit 112 supports the attachment of one or more disk drives or direct access storage devices 125 (which are typically rotating magnetic disk drive storage devices, although they could alternatively be other storage devices, including arrays of disk drives configured to appear as a single large storage device to a host computer). In another embodiment, the storage device 125 may be implemented via any type of secondary storage device. The contents of the memory 102, or any portion thereof, may be stored to and retrieved from the storage device 125, as needed. The I/O device interface 113 provides an interface to any of various other input/output devices or devices of other types, such as printers, fax machines, the internal corrosion sensor 126, the fan 128, the external wind sensor 190, and the external corrosion sensor 192. The network adapter 114 provides one or more communications paths from the computer system 100 to other digital devices and computer systems; such paths may comprise, e.g., one or more networks 130.

Although the memory bus 103 is shown in FIG. 1 as a relatively simple, single bus structure providing a direct communication path among the processors 101, the memory 102, and the I/O bus interface unit 105, in fact the memory bus 103 may comprise multiple different buses or communication paths, which may be arranged in any of various forms, such as point-to-point links in hierarchical, star or web configurations, multiple hierarchical buses, parallel and redundant paths, or any other appropriate type of configuration. Furthermore, while the I/O bus interface unit 105 and the I/O bus 104 are shown as single respective units, the computer system 100 may, in fact, contain multiple I/O bus interface units 105 and/or multiple I/O buses 104. While multiple I/O interface units are shown, which separate the system I/O bus 104 from various communications paths running to the various I/O devices, in other embodiments some or all of the I/O devices are connected directly to one or more system I/O buses.

The internal corrosion sensor 126 senses or detects corrosive agents in the air internal to the computer 100 and reports the amount of the detected corrosive agents over time. In an embodiment, the corrosion sensor 126 comprises a conductive material, e.g., a silver filament, which corrodes over time, in response to the action of the airborne corrosive agents. In response to the corrosion, the electrical resistance of the conductive material changes over time, as less and less of the conductive material remains, and the internal corrosion sensor 126 reports the changing resistance, over time, to the executing controller 150, via the I/O device interface 113. In other embodiments, any appropriate corrosion sensor may be used.

The fan 128 comprises rotating vanes or blades, which cause air to move. The fan 128 may be powered by an electrical motor that operates at variable speeds, to provide variable airflow and cooling power. The fan 128 operates to cool the computer 100 by drawing cooler air into the computer 100 from the outside, by expelling warm air from inside of the computer 100 to the outside, or by moving air across a heat sink or electrical component, in order to cool the computer 100 via heat conduction.

The wind sensor 190 is external to the computer 100 and senses or measures and reports the external wind speed and external wind direction to the computer 100. The wind sensor 190 may be implemented as an ultrasonic wind sensor, but in other embodiments any appropriate type of wind sensor may be used. The wind sensor 190 may be implemented as a single unit that measures both wind speed and wind direction or as separate units that measure wind speed and wind direction, individually. A wind sensor that measures wind speed is also known as an anemometer and in various embodiments is implemented as a cup anemometer, a plate anemometer, a sonic anemometer, a laser Doppler anemometer, a hot wire anemometer, or any other appropriate type of anemometer.

The external corrosion sensor 192 is disposed external to, or outside of, the computer 100. In various embodiments, the external sensor 192 may be within the building that houses the computer 100 or may be outside of the building. In various embodiments, the external corrosion sensor 192 may be of the same type and construction as the internal corrosion sensor 126 or a different type and construction.

In various embodiments, the computer system 100 is a multi-user mainframe computer system, a single-user system, or a server computer or similar device that has little or no direct user interface, but receives requests from other computer systems (clients). In other embodiments, the computer system 100 is implemented as a desktop computer, portable computer, laptop or notebook computer, tablet computer, pocket computer, telephone, smart phone, pager, automobile, teleconferencing system, appliance, or any other appropriate type of electronic device.

The network 130 may be any suitable network or combination of networks and may support any appropriate protocol suitable for communication of data and/or code to/from the computer system 100. In various embodiments, the network 130 may represent a storage device or a combination of storage devices, either connected directly or indirectly to the computer system 100. In another embodiment, the network 130 may support wireless communications. In another embodiment, the network 130 may support hard-wired communications, such as a telephone line or cable. In another embodiment, the network 130 may be the Internet and may support IP (Internet Protocol). In another embodiment, the network 130 is implemented as a local area network (LAN) or a wide area network (WAN). In another embodiment, the network 130 is implemented as a hotspot service provider network. In another embodiment, the network 130 is implemented an intranet. In another embodiment, the network 130 is implemented as any appropriate cellular data network, cell-based radio network technology, or wireless network. In another embodiment, the network 130 is implemented as any suitable network or combination of networks. Although one network 130 is shown, in other embodiments any number of networks (of the same or different types) may be present.

FIG. 1 is intended to depict the representative major components of the computer system 100, the network 130, the wind sensor 190, and the external corrosion sensor 192. But, individual components may have greater complexity than represented in FIG. 1, components other than or in addition to those shown in FIG. 1 may be present, and the number, type, and configuration of such components may vary. Several particular examples of such additional complexity or additional variations are disclosed herein; these are by way of example only and are not necessarily the only such variations. The various program components illustrated in FIG. 1 and implementing various embodiments of the invention may be implemented in a number of manners, including using various computer applications, routines, components, programs, objects, modules, data structures, etc., and are referred to hereinafter as "computer programs," or simply "programs."

The computer programs comprise one or more instructions or statements that are resident at various times in various memory and storage devices in the computer system 100 and that, when read and executed by one or more processors in the computer system 100 or when interpreted by instructions that are executed by one or more processors, cause the computer system 100 to perform the actions necessary to execute steps or elements comprising the various aspects of embodiments of the invention. Aspects of embodiments of the invention may be embodied as a system, method, or computer program product. Accordingly, aspects of embodiments of the invention may take the form of an entirely hardware embodiment, an entirely program embodiment (including firmware, resident programs, micro-code, etc., which are stored in a storage device) or an embodiment combining program and hardware aspects that may all generally be referred to herein as a "circuit," "module," or "system." Further, embodiments of the invention may take the form of a computer program product embodied in one or more computer-readable medium(s) having computer-readable program code embodied thereon.

Any combination of one or more computer-readable medium(s) may be utilized. The computer-readable medium may be a computer-readable signal medium or a computer-readable storage medium. A computer-readable storage medium, may be, for example, but not limited to, an electronic, magnetic, optical, electromagnetic, infrared, or semiconductor system, apparatus, or device, or any suitable combination of the foregoing. More specific examples (an non-exhaustive list) of the computer-readable storage media may comprise: an electrical connection having one or more wires, a portable computer diskette, a hard disk (e.g., the storage device 125), a random access memory (RAM) (e.g., the memory 102), a read-only memory (ROM), an erasable programmable read-only memory (EPROM) or Flash memory, an optical fiber, a portable compact disc read-only memory (CD-ROM), an optical storage device, a magnetic storage device, or any suitable combination of the foregoing. In the context of this document, a computer-readable storage medium may be any tangible medium that can contain, or store, a program for use by or in connection with an instruction execution system, apparatus, or device.

A computer-readable signal medium may comprise a propagated data signal with computer-readable program code embodied thereon, for example, in baseband or as part of a carrier wave. Such a propagated signal may take any of a variety of forms, including, but not limited to, electro-magnetic, optical, or any suitable combination thereof. A computer-readable signal medium may be any computer-readable medium that is not a computer-readable storage medium and that communicates, propagates, or transports a program for use by, or in connection with, an instruction execution system, apparatus, or device. Program code embodied on a computer-readable medium may be transmitted using any appropriate medium, including but not limited to, wireless, wire line, optical fiber cable, Radio Frequency, or any suitable combination of the foregoing.

Computer program code for carrying out operations for aspects of embodiments of the present invention may be written in any combination of one or more programming languages, including object oriented programming languages and conventional procedural programming languages. The program code may execute entirely on the user's computer, partly on a remote computer, or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of embodiments of the invention are described below with reference to flowchart illustrations and/or block diagrams of methods, apparatus (systems), and computer program products. Each block of the flowchart illustrations and/or block diagrams, and combinations of blocks in the flowchart illustrations and/or block diagrams may be implemented by computer program instructions embodied in a computer-readable medium. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified by the flowchart and/or block diagram block or blocks. These computer program instructions may also be stored in a computer-readable medium that can direct a computer, other programmable data processing apparatus, or other devices to function in a particular manner, such that the instructions stored in the computer-readable medium produce an article of manufacture, including instructions that implement the function/act specified by the flowchart and/or block diagram block or blocks.

The computer programs defining the functions of various embodiments of the invention may be delivered to a computer system via a variety of tangible computer-readable storage media that may be operatively or communicatively connected (directly or indirectly) to the processor or processors. The computer program instructions may also be loaded onto a computer, other programmable data processing apparatus, or other devices to cause a series of operational steps to be performed on the computer, other programmable apparatus, or other devices to produce a computer-implemented process, such that the instructions, which execute on the computer or other programmable apparatus, provide processes for implementing the functions/acts specified in the flowcharts and/or block diagram block or blocks.

The flowchart and the block diagrams in the figures illustrate the architecture, functionality, and operation of possible implementations of systems, methods, and computer program products, according to various embodiments of the present invention. In this regard, each block in the flowcharts or block diagrams may represent a module, segment, or portion of code, which comprises one or more executable instructions for implementing the specified logical function(s). In some embodiments, the functions noted in the block may occur out of the order noted in the figures. For example, two blocks shown in succession may, in fact, be executed substantially concurrently, or the blocks may sometimes be executed in the reverse order, depending upon the functionality involved. Each block of the block diagrams and/or flowchart illustration, and combinations of blocks in the block diagrams and/or flow chart illustrations, can be implemented by special purpose hardware-based systems that perform the specified functions or acts, in combinations of special purpose hardware and computer instructions.

Embodiments of the invention may also be delivered as part of a service engagement with a client corporation, non-profit organization, government entity, or internal organizational structure. Aspects of these embodiments may comprise configuring a computer system to perform, and deploying computing services (e.g., computer-readable code, hardware, and web services) that implement, some or all of the methods described herein. Aspects of these embodiments may also comprise analyzing the client company, creating recommendations responsive to the analysis, generating computer-readable code to implement portions of the recommendations, integrating the computer-readable code into existing processes, computer systems, and computing infrastructure, metering use of the methods and systems described herein, allocating expenses to users, and billing users for their use of these methods and systems. In addition, various programs described hereinafter may be identified based upon the application for which they are implemented in a specific embodiment of the invention. But, any particular program nomenclature that follows is used merely for convenience, and thus embodiments of the invention are not limited to use solely in any specific application identified and/or implied by such nomenclature. The exemplary environments illustrated in FIG. 1 are not intended to limit the present invention. Indeed, other alternative hardware and/or program environments may be used without departing from the scope of embodiments of the invention.

FIG. 2 depicts a block diagram of an example data structure for corrosion data 152, according to an embodiment of the invention. The corrosion data 152 comprises internal corrosion data 202 and external corrosion data 204. The internal corrosion data 202 comprises entries, each comprising a time field 210, an internal corrosion level field 212, and an internal corrosion difference field 214.

The time field 210, in each entry, specifies the time and/or date at which the values in the internal corrosion level field 212 and the internal corrosion difference field 214, in the same entry, were detected, calculated, determined, or saved to the internal corrosion data 202.

The internal corrosion level field 212, in each entry, specifies the corrosion level detected by the internal corrosion sensor 126 and received by the controller 150 from the internal corrosion sensor 126, at the time specified by the time field 210, in the same entry. In various embodiments, the values in the internal corrosion level field 212 are specified in units of resistance (e.g., ohms) detected by the internal corrosion sensor 126, a percentage of the maximum resistance of the filament of the internal corrosion sensor 126 that the internal corrosion sensor 126 detected at the time 210 in the same entry, a percentage of a filament of the internal corrosion sensor 126 that had been corroded or was missing at the time 210 in the same entry, a percentage of the filament of the internal corrosion sensor 126 that remained at the time 210 in the same entry, or any other appropriate units.

The internal corrosion difference field 214, in each entry, specifies the difference between the value of the internal corrosion level field 212, in the same entry, and the value of the internal corrosion level field 212, in the immediately previous (in time) entry in the internal corrosion data 202. Thus, the internal corrosion difference field 214 specifies the amount of corrosion that has occurred between entries in the internal corrosion data 202. For example, the internal corrosion difference field 214 specifies "0.01" at a time of "8:15" because the internal corrosion level 212 at the same time of "8:15" minus the internal corrosion level 212 of "0.1" at the immediately previous time (within the internal corrosion data 202) of "8:00" is "0.01."

The external corrosion data 204 comprises entries, each of which comprise a time field 250, an external corrosion level field 252, an external corrosion difference field 254, a wind speed field 256, a wind direction field 258, and a predicted internal corrosion level field 260.

The time field 250, in each entry of the external corrosion data 204, specifies the time and/or date at which the values in the external corrosion level field 252, the external corrosion difference field 254, the wind speed 256, the wind direction 258, and the predicted internal corrosion level field 260, in the same entry, were detected, received, calculated, determined, or saved to the external corrosion data 204.

The external corrosion level field 252, in each entry of the external corrosion data 204, specifies the corrosion level detected by the external corrosion sensor 192 and received by the controller 150 from the external corrosion sensor 192, at the time specified by the time field 250, in the same entry. In various embodiments, the values in the external corrosion level field 252 are specified in units of resistance (e.g., ohms) detected by the external corrosion sensor 192, a percentage of the maximum resistance of the filament of the external corrosion sensor 192 that the external corrosion sensor 192 detected at the time 250 in the same entry, a percentage of a filament of the external corrosion sensor 192 that had been corroded or was missing at the time 250 in the same entry, a percentage of the filament of the external corrosion sensor 192 that remained at the time 250 in the same entry, or any other appropriate units.

The external corrosion difference field 254, in each entry, specifies the difference between the value of the external corrosion level field 252, in the same entry, and the value of the external corrosion level field 252, in the immediately previous (in time) entry. Thus, the external corrosion difference field 254 specifies the amount of corrosion that has occurred between entries in the external corrosion data 204. For example, the external corrosion difference field 254 specifies "0.02" at a time 250 of "8:15" because the external corrosion level 252 of "0.22" at the time 250 of "8:15" minus the external corrosion level 252 of "0.2" at the time 250 of "8:00" is "0.02."

The wind speed field 256, in each entry, specifies the speed or velocity of the wind, as detected by the wind sensor 190, at the time 250, in the same entry. In various embodiments, the wind speed field 256 specifies units in values of miles per hour, kilometers per hour, or any other appropriate units of speed or rate. The wind direction field 258, in each entry, specifies the direction of the wind, as detected by the wind sensor 190, at the time 250, in the same entry. In an embodiment, the wind direction field 258 specifies the direction from which the wind originates. For example, the wind direction 258 that specifies a north (N) wind describes a wind that originates from the north and blows to the south. In various embodiments, the wind direction 258 is specified in cardinal directions, intercardinal directions, ordinal directions, or in azimuth degrees. Thus, for example, a wind originating from the south has azimuth degrees of 180 degrees, and a wind originating from the east has azimuth degrees of 90 degrees.

The predicted internal corrosion level field 260, in each entry, specifies the internal corrosion level that the controller 150 predicted or estimated would occur at the next time after the time 250 of the entry of the predicted internal corrosion level field 260. For example, the predicted internal corrosion level 260 of "0.15" at the time 250 of "8:15" means that the controller 150 estimated or predicted at the time 250 of "8:15" that at the next time 210 of "8:30" the internal corrosion level 212 would be "0.15."

Figure 3:
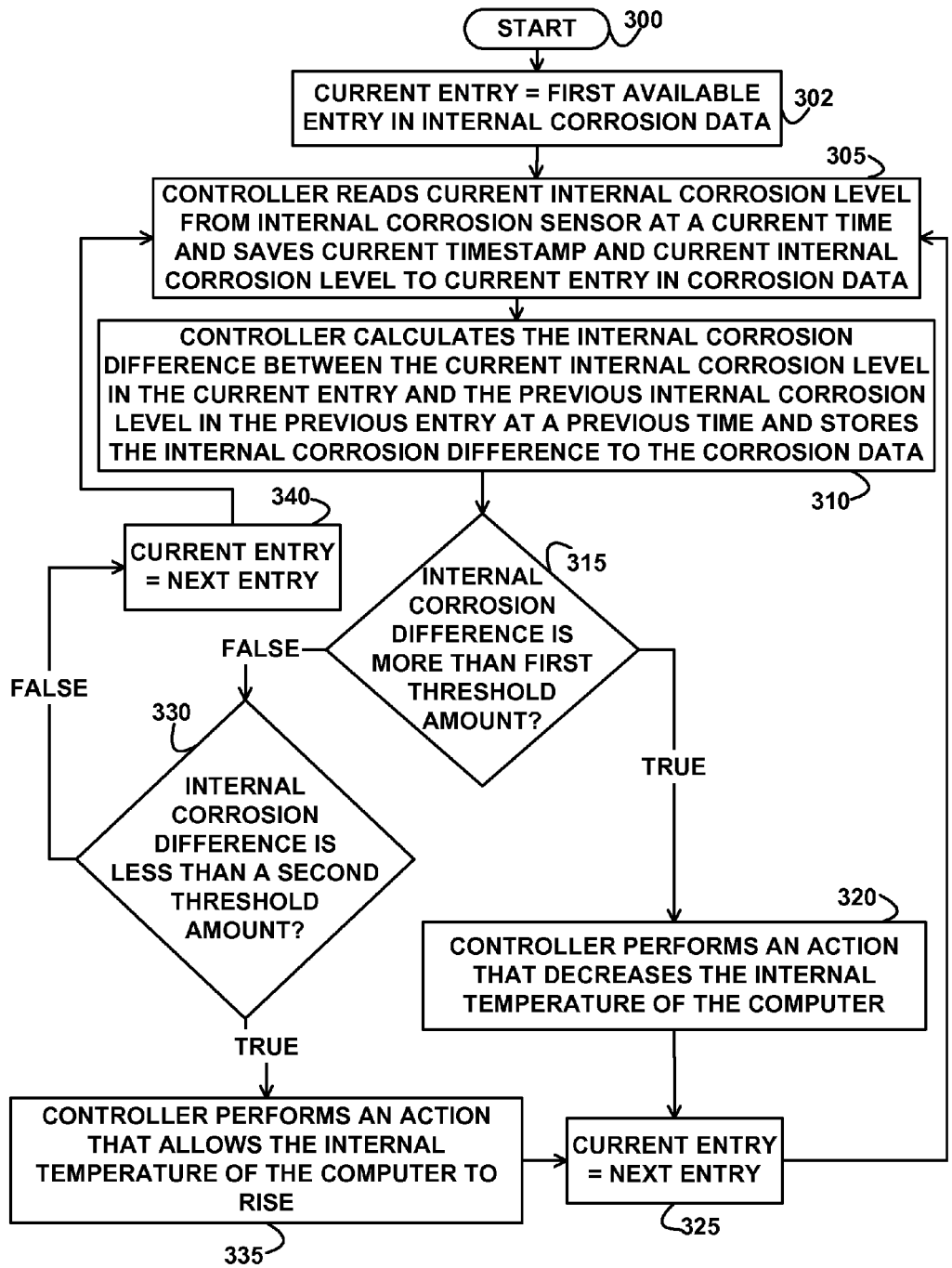
FIG. 3 depicts a flowchart of example processing for responding to an internal corrosion sensor, according to an embodiment of the invention.

FIG. 3 depicts a flowchart of example processing for responding to an internal corrosion sensor, according to an embodiment of the invention. Control begins at block 300. Control then continues to block 302 where the controller 150 sets the current entry to be the first available or unused entry in the internal corrosion data 202. Control then continues to block 305 where the controller 150 reads the current internal corrosion level from the internal corrosion sensor 126 at a current time and saves the current time 210 and the current internal corrosion level 212 to the current entry in the internal corrosion data 202. Control then continues to block 310 where the controller 150 calculates the internal corrosion difference 214 between the current internal corrosion level 212 in the current entry and the previous internal corrosion level in the immediately previous entry at the immediately previous time (i.e., the controller 150 subtracts the previous internal corrosion level from the current internal corrosion level) and stores the internal corrosion difference 214 to the current entry in the internal corrosion data 202. Control then continues to block 315 where the controller 150 determines whether the internal corrosion difference 214 in the current entry is more than a first threshold amount. In an embodiment, the controller 150 receives various threshold amounts from the network 130, from a designer of the controller 150, from the user I/O device 121, or from an application.

If the determination at block 315 is true, then the internal corrosion difference 214 in the current entry is more than the first threshold amount, so control continues to block 320 where the controller 150 performs an action that decreases the internal temperature of the computer 100. In various embodiments, the action may comprise increasing the speed of the fan 128, lowering the clock frequency (down-clocking) of the processor 101, lowering the clock frequency of the memory bus 103, powering off, suspending, or disabling unused cores of the processor 101 or unused chips, unused DIMMs (Dynamic Inline Memory Module) of the memory 102, unused SIMMs (Single Inline Memory Module) of the memory 102, down-clocking, suspending or disabling selected of the interface units 111, 112, 113, and/or 114, or suspending execution of the low priority processes 156, all of which may result in lowering the internal temperature of the computer 100.

Embodiments of the invention may reduce the rate of corrosion of components of the computer 101 because the rate of corrosion (i.e., rate of chemical reaction) is exponentially tied to temperature. Specifically, the Arrhenius equation gives the rate of reaction:

$$k = A e^{-E\_a/(RT)}$$

where E_a is the reaction's activation energy, R is the Universal gas constant (8.314 . . . J/mol K), e is the natural logarithm base (2.7182 . . . ), T is temperature in Kelvin units, and A is a pre-exponential factor (in chemical kinetics, A is the frequency of molecule collisions in (seconds)$^{-1}$). By lowering the value of T (the temperature in Kelvin), the rate of corrosion k drops exponentially. Embodiments of the invention increase the value of A linearly by increasing the air flow in the computer 100, but the corresponding reduction in T more than compensates for this increase.

Control then continues to block 325 where the controller 150 sets the current entry to be the next available entry in the internal corrosion data 202. Control then returns to block 305, as previously described above.

If the determination at block 315 is false, then the internal corrosion difference 214 in the current entry is not more than (is less than or equal to) the first threshold amount, so control continues to block 330 where the controller 150 determines whether the internal corrosion difference 214 in the current entry is less than a second threshold amount, which in various embodiments may be the same or different from the first threshold amount.

If the determination at block 330 is true, then the internal corrosion difference 214 in the current entry is less than the second threshold amount, so control continues to block 335 where the controller 150 performs an action that allows the internal temperature of the computer 100 to increase. In various embodiments, actions that allow the internal temperature to increase comprise decreasing the speed of the fan 128, increasing the clock frequency of the processor 101, increasing the clock frequency of the memory bus 103, powering on or starting cores of the processor 101 or chips, DIMMs, or SIMMs of the memory 102, raising the clock frequency or powering on selected of the interface units 111, 112, 113, and/or 114, or starting execution of the low priority processes 156. Control then continues to block 325, as previously described above.

If the determination at block 330 is false, then the internal corrosion difference 214 in the current entry is not less than (is greater than or equal to) the second threshold amount, so control continues to block 340 where the controller 150 sets the current entry to be next available or unused entry in the internal corrosion data 202. Control then returns to block 305, as previously described above.

Figure 4:
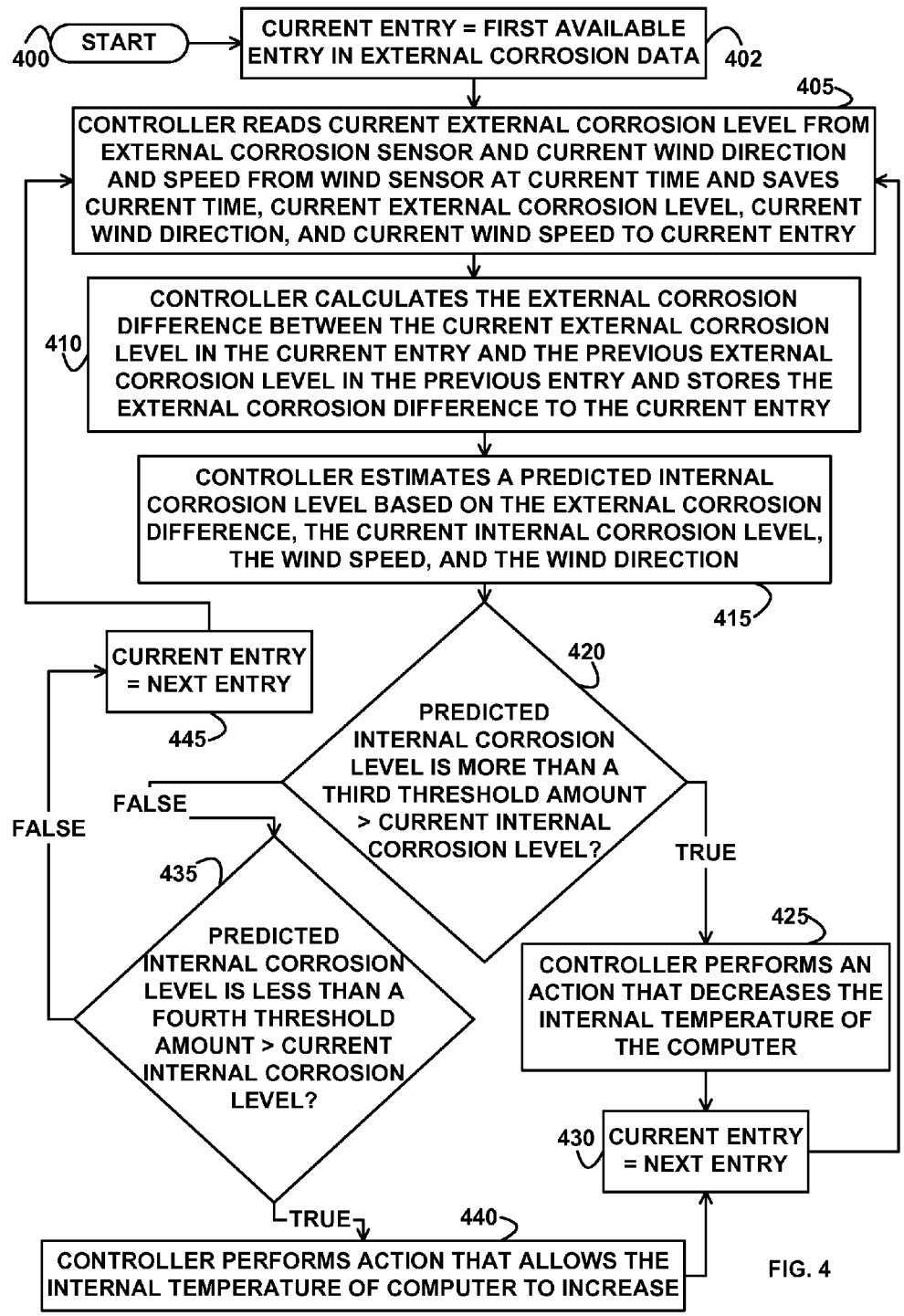
FIG. 4 depicts a flowchart of example processing for responding to an external corrosion sensor, according to an embodiment of the invention.

FIG. 4 depicts a flowchart of example processing for responding to an external corrosion sensor, according to an embodiment of the invention. In various embodiments, the processing of FIGS. 3 and 4 execute concurrently, substantially concurrently, or interleaved on the same or different processors via time slicing, multi-processing, multi-threading, or multi-programming techniques. Control begins at block 400. Control then continues to block 402 where the controller 150 initializes the current entry in the external corrosion data 204 to be the first available or unused entry in the external corrosion data 204. Control then continues to block 405 where the controller 150 reads the current external corrosion level from the external corrosion sensor 192 at the current time, reads the current wind direction and wind speed from the wind sensor 190 at the current time, and saves the current time, the current external corrosion level 252, the current wind direction 258, and the current wind speed 256 to the current entry in the external corrosion data 204.

Control then continues to block 410 where the controller 150 calculates the external corrosion difference 254 between the current external corrosion level 252 in the current entry and the previous external corrosion level 252 in the immediately previous entry at the immediately previous time 250 and stores the external corrosion difference 254 to the current entry in the external corrosion data 204. Control then continues to block 415 where the controller 150 estimates a predicted internal corrosion level 260 based on the external corrosion difference 254 at the current time 250, the current internal corrosion level 212 at the current time 210, the current wind speed 256 at the current time 250, the current wind direction 258 at the current time 250, and the historical values of the wind speed 256, the wind direction 258, and internal and external corrosion levels at previous times that are before the current time.

In an embodiment, the controller 150 estimates the predicted internal corrosion level 260 by selecting a previous (in time) wind speed 256 and previous (in time) wind direction 258 that most closely match the current wind speed 256 and current wind direction 258. The previous wind speed 256 and previous wind direction 258 were detected by the wind sensor 190 at a previous time, and the previous time is before the current time. In an embodiment, the controller 150 determines that the previous wind speed 256 and previous wind direction 258 most closely match the current wind speed 256 and current wind direction 258 by, for each previous entry, calculating the absolute value of the difference between the current wind speed 256 and the previous wind speed 256, and adding the result to the absolute value of the difference between the previous wind direction 258 and the current wind direction 258 (in degrees). The controller 150 then determines the entry in the external corrosion data 204 whose sum of the absolute values is the smallest. In an embodiment, the controller 150 multiplies the absolute values by weight values, which are set by the designer of the controller 150 or received from the network 130, from the user I/O device 121, or from an application. The controller 150 further determines a previous external corrosion difference 254 that was detected at the previous time of the selected entry and determines a next internal corrosion difference 214 that was detected at an immediately next time after the previous time of the selected entry. The controller 150 then divides the next internal corrosion difference 214 by the previous external corrosion difference 254 to yield a result and adds the result to the current internal corrosion level 212 to yield the predicted internal corrosion level 260, which the controller saves to the current entry in the external corrosion data 204.

Control then continues to block 420 where the controller 150 determines whether the current predicted internal corrosion level 260 at the current time 250 is greater than the current internal corrosion level 212 at the current time 210 by more than a third threshold amount. If the determination at block 420 is true, then the predicted internal corrosion level 260 is greater than the current internal corrosion level 212 at the current time by more than a third threshold amount, so control continues to block 425 where the controller 150 performs an action that decreases the internal temperature of the computer 100. In various embodiments, the action performed by the logic of block 425 that decreases the internal temperature of the computer 100 may be the same or different from the actions performed by the logic of FIG. 3 that decrease the internal temperature of the computer 100. Control then continues to block 430 where the controller 150 sets the current entry to be the next available or unused entry in the external corrosion data 204. Control then returns to block 405, as previously described above.

If the determination at block 420 is false, then the current predicted internal corrosion level 260 is not greater than the current internal corrosion level 212 at the current time by more than the third threshold amount, so control continues to block 435 where the controller 150 determines whether the predicted internal corrosion level 260 is less than the current internal corrosion level 212 by more than a fourth threshold amount.

If the determination at block 435 is true, then the predicted internal corrosion level 260 is less than the current internal corrosion level 212 by more than the fourth threshold amount, so control continues to block 440 where the controller 150 performs an action that allows the internal temperature of the computer 100 to increase. In various embodiments, the action performed by the processing of block 440 is the same different than the actions of FIG. 3 that allow the internal temperature of the computer 100 to increase. Control then continues to block 430 where the controller 150 sets the current entry to be the next available or unused entry in the external corrosion data 204. Control then returns to block 405, as previously described above.

If the determination at block 435 is false, then the predicted internal corrosion level 260 is not greater than current internal corrosion level 212 by less than the fourth threshold amount, so control continues to block 445 where the controller 150 sets the current entry in the external corrosion data 204 to be the next available or unused entry in the external corrosion data 204. Control then returns to block 405, as previously described above.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises" and/or "comprising," when used in this specification, specify the presence of the stated features, integers, steps, operations, elements, and/or components, but do not preclude the presence or addition of one or more other features, integers, steps, operations, elements, components, and/or groups thereof. In the previous detailed description of exemplary embodiments of the invention, reference was made to the accompanying drawings (where like numbers represent like elements), which form a part hereof, and in which is shown by way of illustration specific exemplary embodiments in which the invention may be practiced. These embodiments were described in sufficient detail to enable those skilled in the art to practice the invention, but other embodiments may be utilized and logical, mechanical, electrical, and other changes may be made without departing from the scope of the present invention. In the previous description, numerous specific details were set forth to provide a thorough understanding of embodiments of the invention. But, embodiments of the invention may be practiced without these specific details. In other instances, well-known circuits, structures, and techniques have not been shown in detail in order not to obscure embodiments of the invention.

Different instances of the word "embodiment" as used within this specification do not necessarily refer to the same embodiment, but they may. Any data and data structures illustrated or described herein are examples only, and in other embodiments, different amounts of data, types of data, fields, numbers and types of fields, field names, numbers and types of rows, records, entries, or organizations of data may be used. In addition, any data may be combined with logic, so that a separate data structure is not necessary. The previous detailed description is, therefore, not to be taken in a limiting sense.

What is claimed is:
1. A method comprising:
reading a current internal corrosion level at a current time from an internal corrosion sensor that is internal to a computer;
calculating an internal corrosion difference between the current internal corrosion level and a previous internal corrosion level;

if the internal corrosion difference is more than a first threshold amount, performing a first action that decreases an internal temperature of the computer;

if the internal corrosion difference is less than a second threshold amount, performing a second action that allows the internal temperature of the computer to increase;

reading a current external corrosion level at the current time from an external corrosion sensor that is external to the computer;

reading a current wind speed and current wind direction at the current time from a wind sensor that is external to the computer;

calculating a current external corrosion difference between the current external corrosion level and a previous external corrosion level; and estimating a predicted internal corrosion level based on the current external corrosion difference, the current internal corrosion level, the current wind speed, and the current wind direction.

2. The method of claim 1, further comprising:
if the predicted internal corrosion level is greater than the current internal corrosion level by more than a third threshold amount, performing a third action that decreases the internal temperature of the computer.

3. The method of claim 1, further comprising:
if the predicted internal corrosion level is greater than the current internal corrosion level by less than a fourth threshold amount, performing a fourth action that allows the internal temperature of the computer to increase.

4. The method of claim 1, wherein the estimating the predicted internal corrosion level further comprises:
finding a previous wind speed and previous wind direction that most closely match the current wind speed and current wind direction, wherein the previous wind speed and previous wind direction were detected by the wind sensor at a previous time, wherein the previous time is before the current time; and
determining a previous external corrosion difference that was detected at the previous time.

5. The method of claim 4, wherein the estimating the predicted internal corrosion level further comprises:
determining a next internal corrosion difference that was detected at a next time after the previous time.

6. The method of claim 5, wherein the estimating the predicted internal corrosion level further comprises:
dividing the next internal corrosion difference by the previous external corrosion difference to yield a result and adding the result to the current internal corrosion level to yield the predicted internal corrosion level.

7. A non-transitory computer-readable storage medium encoded with instructions, wherein the instructions when executed comprise:
reading a current internal corrosion level at a current time from an internal corrosion sensor that is internal to a computer;
calculating an internal corrosion difference between the current internal corrosion level and a previous internal corrosion level;
if the internal corrosion difference is more than a first threshold amount, performing a first action that decreases an internal temperature of the computer;
if the internal corrosion difference is less than a second threshold amount, performing a second action that allows the internal temperature of the computer to increase;
reading a current external corrosion level at the current time from an external corrosion sensor that is external to the computer;
reading a current wind speed and current wind direction at the current time from a wind sensor that is external to the computer;
calculating a current external corrosion difference between the current external corrosion level and a previous external corrosion level; and
estimating a predicted internal corrosion level based on the current external corrosion difference, the current internal corrosion level, the current wind speed, and the current wind direction.

8. The non-transitory computer-readable storage medium of claim 7, further comprising:
if the predicted internal corrosion level is greater than the current internal corrosion level by more than a third threshold amount, performing a third action that decreases the internal temperature of the computer.

9. The non-transitory computer-readable storage medium of claim 7, further comprising:
if the predicted internal corrosion level is greater than the current internal corrosion level by less than a fourth threshold amount, performing a fourth action that allows the internal temperature of the computer to increase.

10. The non-transitory computer-readable storage medium of claim 9, wherein the estimating the predicted internal corrosion level further comprises:
finding a previous wind speed and previous wind direction that most closely match the current wind speed and current wind direction, wherein the previous wind speed and previous wind direction were detected by the wind sensor at a previous time, wherein the previous time is before the current time; and
determining a previous external corrosion difference that was detected at the previous time.

11. The non-transitory computer-readable storage medium of claim 10, wherein the estimating the predicted internal corrosion level further comprises:
determining a next internal corrosion difference that was detected at a next time after the previous time.

12. The non-transitory computer-readable storage medium of claim 11, wherein the estimating the predicted internal corrosion level further comprises:
dividing the next internal corrosion difference by the previous external corrosion difference to yield a result and adding the result to the current internal corrosion level to yield the predicted internal corrosion level.

13. A computer comprising:
a processor;
an internal corrosion sensor communicatively connected to the processor, wherein the internal corrosion sensor detects airborne corrosive agents that are internal to the computer; and
memory communicatively connected to the processor, wherein the memory is encoded with instructions, and wherein the instructions when executed by the processor comprise
reading a current internal corrosion level at a current time from the internal corrosion sensor that is internal to the computer,
calculating an internal corrosion difference between the current internal corrosion level and a previous internal corrosion level,
if the internal corrosion difference is more than a first threshold amount, performing a first action that decreases an internal temperature of the computer, if the internal corrosion difference is less than a second threshold amount, performing a second action that allows the internal temperature of the computer to increase, reading a current external corrosion level at the current time from an external corrosion sensor that is external to the computer, wherein the external corrosion sensor detects airborne corrosive agents that are external to the computer, reading a current wind speed and current wind direction at the current time from a wind sensor that is external to the computer, calculating a current external corrosion difference between the current external corrosion level and a previous external corrosion level, and estimating a predicted internal corrosion level based on the current external corrosion difference, the current internal corrosion level, the current wind speed, and the current wind direction.

14. The computer of claim 13, wherein the instructions further comprise:

if the predicted internal corrosion level is greater than the current internal corrosion level by more than a third threshold amount, performing a third action that decreases the internal temperature of the computer.

15. The computer of claim 14, wherein the instructions further comprise:

if the predicted internal corrosion level is greater than the current internal corrosion level by less than a fourth threshold amount, performing a fourth action that allows the internal temperature of the computer to increase.

16. The computer of claim 15, wherein the estimating the estimating the predicted internal corrosion level further comprises:

finding a previous wind speed and previous wind direction that most closely match the current wind speed and current wind direction, wherein the previous wind speed and previous wind direction were detected by the wind sensor at a previous time, wherein the previous time is before the current time;

determining a previous external corrosion difference that was detected at the previous time; and determining a next internal corrosion difference that was detected at a next time after the previous time.

17. The computer of claim 16, wherein the estimating the predicted internal corrosion level further comprises:

dividing the next internal corrosion difference by the previous external corrosion difference to yield a result and adding the result to the current internal corrosion level to yield the predicted internal corrosion level.

\* \* \* \* \*